US008470336B2

(12) United States Patent
Kroll (10) Patent No.: US 8,470,336 B2
(45) Date of Patent: *Jun. 25, 2013

(54) **VACCINATION OF YOUNG ANIMALS AGAINST *LAWSONIA INTRACELLULARIS* INFECTIONS**

(75) Inventor: Jeremy Kroll, Urbandale, IA (US)

(73) Assignee: Boehringer Ingelheim Vetmedica, Inc., Saint Joseph, MO (US)

(*) Notice: Subject to any disclaimer, the term of this patent is extended or adjusted under 35 U.S.C. 154(b) by 125 days.

This patent is subject to a terminal disclaimer.

(21) Appl. No.: 11/750,458

(22) Filed: May 18, 2007

(65) Prior Publication Data

US 2008/0063648 A1 Mar. 13, 2008

Related U.S. Application Data

(60) Provisional application No. 60/803,207, filed on May 25, 2006.

(51) Int. Cl.
*A61K 39/02* (2006.01)

(52) U.S. Cl.
USPC ..... 424/234.1; 424/93.4; 424/825; 435/252.1

(58) Field of Classification Search
None
See application file for complete search history.

(56) References Cited

U.S. PATENT DOCUMENTS

| | | | |
|---|---|---|---|
| 3,479,430 A | 11/1969 | Welter | |
| 3,907,987 A | 9/1975 | Wilson | |
| 4,132,597 A | 1/1979 | Kvanta | |
| 4,237,218 A | 12/1980 | Monthony et al. | |
| 4,880,739 A | 11/1989 | Yamada et al. | |
| 4,904,597 A | 2/1990 | Inoue et al. | |
| 4,920,048 A | 4/1990 | Diderichsen | |
| 5,126,265 A | 6/1992 | Cidaria et al. | |
| 5,192,679 A | 3/1993 | Dawson et al. | |
| 5,230,912 A | 7/1993 | Yajima et al. | |
| 5,296,221 A | 3/1994 | Mitsuoka et al. | |
| 5,318,908 A | 6/1994 | Seki et al. | |
| 5,338,670 A | 8/1994 | Sekura et al. | |
| 5,380,657 A | 1/1995 | Schaefer et al. | |
| 5,436,001 A | 7/1995 | Kramer | |
| 5,610,059 A | 3/1997 | Joens et al. | |
| 5,714,375 A | 2/1998 | Knittel et al. | |
| 5,885,823 A * | 3/1999 | Knittel et al. | 435/243 |
| 6,414,036 B1 | 7/2002 | Ninkov | |
| 6,605,696 B1 | 8/2003 | Rosey | |
| 6,649,660 B2 | 11/2003 | Ninkov | |
| 6,921,536 B2 | 7/2005 | Jacobs et al. | |
| 6,982,314 B2 | 1/2006 | Rosey | |
| 7,022,328 B1 | 4/2006 | Panaccio et al. | |
| 7,052,697 B1 | 5/2006 | Hasse et al. | |
| 7,312,065 B2 | 12/2007 | Roof et al. | |
| 7,550,270 B2 | 6/2009 | Kroll et al. | |
| 7,758,870 B2 | 7/2010 | Roof et al. | |
| 2002/0103261 A1 | 8/2002 | Ninkov | |
| 2003/0021802 A1 * | 1/2003 | Rosey | 424/190.1 |
| 2003/0087421 A1 | 5/2003 | Gebhart et al. | |
| 2003/0157120 A1 | 8/2003 | Panaccio et al. | |
| 2005/0031647 A1 | 2/2005 | Roof et al. | |
| 2005/0069559 A1 | 3/2005 | Jacobs et al. | |
| 2005/0143561 A1 | 6/2005 | Rosey | |
| 2006/0024696 A1 | 2/2006 | Kapur et al. | |
| 2006/0171960 A1 | 8/2006 | Chu et al. | |
| 2006/0204522 A1 | 9/2006 | Kroll et al. | |
| 2006/0286118 A1 | 12/2006 | Vermeij | |
| 2007/0014815 A1 * | 1/2007 | Kroll et al. | 424/234.1 |
| 2007/0212373 A1 | 9/2007 | Vermeij | |
| 2008/0063648 A1 | 3/2008 | Kroll | |
| 2008/0112980 A1 | 5/2008 | Roof et al. | |
| 2008/0226669 A1 | 9/2008 | Roof et al. | |
| 2008/0241190 A1 | 10/2008 | Kroll et al. | |
| 2008/0279893 A1 | 11/2008 | Vaughn et al. | |
| 2009/0215698 A1 | 8/2009 | Schaeffer et al. | |
| 2010/0062021 A1 | 3/2010 | Winkelman | |
| 2010/0266637 A1 | 10/2010 | Deitmer et al. | |

FOREIGN PATENT DOCUMENTS

| | | |
|---|---|---|
| EP | 1219711 A2 | 7/2002 |
| EP | 1403643 A1 | 3/2004 |
| EP | 1586646 A2 | 10/2005 |
| WO | 9407531 A1 | 4/1994 |
| WO | 9639629 A1 | 12/1996 |
| WO | 9720050 A1 | 6/1997 |
| WO | 0189559 A2 | 11/2001 |
| WO | 0226250 A2 | 4/2002 |
| WO | 03006665 A1 | 1/2003 |
| WO | 2004033631 A2 | 4/2004 |
| WO | 2005011731 A1 | 2/2005 |
| WO | 2005070958 A2 | 8/2005 |
| WO | 2006020730 A2 | 2/2006 |

(Continued)

OTHER PUBLICATIONS

Product information for Enterisol SC-54 dated May 2003.*
Love et al., "Pathology of Proliferative Haemorrhagic Enteropathy in Pigs". Veterinary Pathology, vol. 16, 1979, pp. 41-48.
McCluskey et al., "LsaA, an Antigen Involved in Cell Attachment and Invasion, Is Expressed by *Lawsonia intracellularis* during Infection In Vitro and In Vivo". Infection and Immunity, vol. 70, No. 6, Jun. 2002, pp. 2899-2907.
McOrist et al., "Antimicrobial Susceptibility of Ileal Symbiont Intracellularis Isolated from Pigs with Proliferative Enteropathy". Journal of Clinical Microbiology, vol. 33, No. 5, May 1995, pp. 1314-1317.
McOrist et al., "Characterization of *Lawsonia intracellularis* gen. nov., sp. nov., the Obligately Intracellular Bacterium of Porcine Proliferative Enteropathy". International Journal of Systematic Bacteriology, vol. 45, No. 4, Oct. 1995, pp. 820-825.

(Continued)

*Primary Examiner* — Oluwatosin Ogunbiyi
(74) *Attorney, Agent, or Firm* — Michael P. Morris; Joyce L. Morrison (57) ABSTRACT

The present invention provides a method of vaccinating a young animal against *L. intracellularis* infection comprising the step of administering to an animal an effective dose of *L. intracellularis* antigen. It also provides a method of vaccinating an animal, preferably a young animal, having anti-*L. intracellularis* antibodies or is exposed to anti-*L. intracellularis* antibodies. In particular, those anti-*L.intracellularis* antibodies are maternally derived antibodies.

11 Claims, 1 Drawing Sheet

FOREIGN PATENT DOCUMENTS

| | | | |
|---|---|---|---|
| WO | 2006099561 | A1 | 9/2006 |
| WO | 2006113782 | A2 | 10/2006 |
| WO | 2006116763 | A2 | 11/2006 |
| WO | 2007011993 | A1 | 1/2007 |
| WO | 2007140244 | A2 | 12/2007 |
| WO | 2008063959 | A1 | 5/2008 |
| WO | 2009037262 | A2 | 3/2009 |

OTHER PUBLICATIONS

McOrist et al., "Control of porcine proliferative enteropathy by oral administration of chlortetracycline". The Veterinary Record, vol. 144, Jan. 1999, pp. 48-49.

McOrist et al., "Early Lesions of Proliferative Enteritis in Pigs and Hamsters". Veterinary Pathology, vol. 26, No. 3, May 1989, pp. 260-264.

McOrist et al., "Entry of the bacterium ileal symbiont *intracellularis* into cultured enterocytes and its subsequent release". Research in Veterinary Science, vol. 59, 1995, pp. 255-260.

McOrist et al., "In Vitro and In-Life Studies of Efficacy of Valnemulin for Proliferative Enteropathy (ILEITIS)". Proceedings of the 15th IPVS Congress, Birmingham, England, Jul. 1998, p. 114.

McOrist et al., "In vitro testing of antimicrobial agents for proliferative enteropathy (ileitis)". Swine Health and Production, vol. 3, No. 4, Jul. and Aug. 1995, pp. 146-149.

McOrist et al., "Monoclonal antibodies to intracellular *campylobacter*-like organisms of the porcine proliferative enteropathies". The Veterinary Record, vol. 121, No. 18, Oct. 1987, pp. 421-422.

McOrist et al., "Oral administration of tylosin phosphate for treatment and prevention of proliferative enteropathy in pigs". Advanced Journal of Veterinary Research, vol. 58, No. 2, Feb. 1997, pp. 136-139.

McOrist et al., "Polymerase chain reaction for diagnosis of porcine proliferative enteropathy". Veterinary Microbiology, vol. 41, No. 3, 1994, pp. 205-212.

McOrist et al., "Porcine Proliferative Enteropathy". The Veterinary Record, vol. 132, No. 14, Apr. 1993, p. 368.

McOrist et al., "Reproduction of Porcine Proliferative Enteropathy with Pure Cultures of Ileal Symbiont *Intracellularis*". Infection and Immunity, vol. 61, No. 10, Oct. 1993, pp. 4286-4292.

McOrist et al., "Synergism of ileal symbiont *intracellularis* and gut bacteria in the reproduction of porcine proliferative enteropathy". The Veterinary Record, vol. 134, No. 13, Mar. 1994, pp. 331-332.

McOrist et al., "The Treatment of Induced Porcine Proliferative Enteropathy (ILEITIS) with Tylosin Tartrate (Tylan® Soluble, Elanco) Administered Via Drinking Water". Proceedings of the 15th IPVS Congress, Birmingham, England, Jul. 1998, p. 118.

McOrist et al., "Treatment and prevention of porcine proliferative enteropathy with oral tiamulin". The Veterinary Record, vol. 139, Dec. 1996, pp. 615-618.

Nelson, J.B., "The Maternal Transmission of vaccinial Immunity in Swine". The Journal of Experimental Medicine, vol. 56, 1932, pp. 835-840.

Nelson, J.B., "The Maternal Transmission of Vaccinial Immunity in Swine". The Journal of Experimental Medicine, vol. 60, 1934, pp. 287-291.

Nielsen et al., ":The serological response to *Salmonella* serovars typhimurium and infantis in experimentally infected pigs. The time course followed with an indirect anti-LPS ELISA and bacteriological examinations". Veterinary Microbiology, vol. 47, 1995, pp. 205-218.

Oka et al., "Large-Scale Animal Cell Culture: A Biological Perspective". Large-Scale Mammalian Cell Culture, Marcel Dekker, Inc., New York and Basel, 1990, pp. 71-73.

Peace et al., "Comparative Analysis of the 16S rRNA Gene Sequence of the Putative Agent of Proliferative Ileitis of Hamsters". International Journal of Systematic Bacteriology, vol. 44, No. 4, Oct. 1994, pp. 832-835.

Pensaert et al., "Viremia and effect of fetal infection with porcine viruses with special reference to porcine circovirus 2 infection". Veterinary Microbiology, vol. 98, 2004, pp. 175-183.

Pozo et al., "Study of *Lawsonia intracellularis* Infection in Breeding Stock and Suckling Pigs". Proceedings of the 17th IPVS Congress, Ames, Iowa, 2002, vol. 2, p. 205.

Product Insert for Enterisol Ileitis®, Boehringer Ingelheim Vetmedica, Inc., Jan. 2005, 2 pages.

Reuveny, S., "Microcarrier Culture Systems". Bioprocess Technology, vol. 10, 1990, pp. 271-341.

Reuveny, S., "Microcarriers in Cell Culture Structure and Applications". Advances in Cell Culture, vol. 4, 1985, pp. 213-247.

Rowland et al., "Intestinal Adenomatosis in the Pig: Occurrence of a Bacterium in Affected Cells". Nature, vol. 243, Jun. 1973, p. 417.

Rowland et al., Porcine intestinal adenomatosis: A possible relationship with necrotic enteritis, regional ileitis and proliferative haemorrhagic enteropathy. Veterinary Records, vol. 97, 1975, pp. 178-180.

Schoeb et al., "Enterocecocolitis Associated with Intraepithelial *Campylobacter*-like Bacteria in Rabbits (*Oryctolagus cuniculus*)". Veterinary Pathology, vol. 27, 1990, pp. 73-80.

Schultheiss, P.C., "A Study of the Pathogenicity of *Campylobacter* Species in Swine". A Thesis Submitted to the Faculty of the Graduate School of the University of Minnesota, Jun. 1987, pp. 1-287.

Senk et al., "Proliferative typhlocolitis—the fifth form of the porcine intestinal adenomatosis complex". Proceedings, International Pig Veterinary Society, 11th Congress, Jul. 1-5, 1990, Lausanne, Switzerlandk, 1990, p. 113.

Spier et al., "Trypsinization of BHK21 Monolayer Cells Grown in Two Large-Scale Unit Process Systems". Biotechnology and Bioengineering, vol. XIX, 1977, pp. 1735-1738.

Starek et al., "Sows Seropositive to *Lawsonia intracellularis* (LI) Influence Performance and LI Seropositivity of their Offspring". Acta Veterinaria BRNO, vol. 73, No. 3, 2004, pp. 341-345.

Stills, H.F., "Isolation of an Intracellular Bacterium from Hamsters (*Mesocricetus auratus*) with Proliferative Ileitis and Reproduction of the Disease with a Pure Culture". Infection and Immunity, vol. 59, No. 9, Sep. 1991, pp. 3227-3236.

Tam et al., "Eukaryotic Cells Grown on Microcarrier Beads Offer a Cost-Efficient Way to Propagate *Chlamydia trachomatis*". BioTechniques, vol. 13, No. 3, 1992, pp. 374-378.

Thacker, E., "Vaccines How They Work, Why They Fail". National Hog Farmer, Apr. 15, 2003. Retrieved online Jun. 16, 2008, 6 pages. http://www.nationalhogfarmer.com/mag/farming_vaccines_work_why/index.html.

Tseneva et al., "Invasiveness and cytotoxicity as criteria in assessing *Yersinia* attenuation". Zhurnal Mikrobiologii, Epidemiologii, i Immunobiologii, vol. 10, No. 6, Sep. 1988, pp. 10-16, Abstract Only.

Walter et al., "Serologic profiling and vaccination timing for *Lawsonia intracellularis*". Journal of Swine Health and Production, vol. 12, No. 6, 2004, pp. 310-313.

Ward et al., "Diagnosing, treating, and controlling proliferative enteritis in swine". Veterinary Medicine, Food-Animal Practice, Mar. 1990, pp. 312-318.

Ward et al., "Reproduction of proliferative enteritis in pigs fed embryonated eggs inoculated with proliferative enteritis tissues". Proceedings, International Pig Veterinary Society, 11th Congress, Jul. 1-5, 1990, Lausanne, Switzerland, p. 116.

Wittmann et al., "Colostral Immunity in Piglets From Sows Vaccinated With Inactivated Aujeszky Disease Virus Vaccine". Archives of Virology, vol. 60, 1979, pp. 33-42.

Wiuff et al., "Immunochemical analyses of serum antibodies from pig herds in a *Salmonella* non-endemic region". Veterinary Microbiology, vol. 85, 2002, pp. 69-82.

Yates et al., "Proliferative Hemorrhagic Enteropathy in Swine: An Outbreak and Review of Literature". Canadian Veterinary Journal, vol. 20, Oct. 1979, pp. 261-268.

"Multicomponent Vaccine Development". NIH Guide, vol. 22, No. 28, Aug. 1993, Retrieved from URL: http://grants.nih.gov/grants/guide/rfa-files/RFA-AI-93-017.html, Retrieved on Nov. 20, 2006, 9 pages.

"Vaccination Guidelines for Swine". Vido Swine Technical Group, Jun. 2004, (obtained on Jan. 6, 2009 from http://www.vido.org/pdf/vstg_pubs/Vaccination%20Guidelines_SWINE_june18.2004-tl1.pdf).

Alderton et al., "Experimental Reproduction of Porcine Proliferative Enteritis". Journal of Comparative Pathology, vol. 106, 1992, pp. 159-167.

Armbruster et al., "Evaluation of Enterisol® LI Ileitis Vaccine and Tylan® Premix Efficacy Against Porcine Proliferative Enteropathy in a Challenge Model". Proceedings of the 18th International Pig Veterinary Society Congress, vol. 2, Hamburg, Germany, 2004, p. 579.

Barna et al., "Effect of gilt seropositivity to *Lawsonia intracellularis* (LI) on their offspring's seropositivity to LI and on diarrhoea after a pure-culture challenge". Preventive Veterinary Medicine, vol. 61, No. 1, Sep. 2003, pp. 71-78.

Birch et al., "Suspension Culture of Mammalian Cells". Large-Scale Mammalian Cell Culture, Marcel Dekker, Inc., New York and Basel, 1990, pp. 258-270.

Boesen et al., "Development, characterization and diagnostic application of a monoclonal antibody specific for a proteinase K resistant *Lawsonia intracellularis* antigen". Veterinary Microbiology, vol. 105, 2006, pp. 199-206.

Boesen et al., "Evaluation of a novel enzyme-linked immunosorbent assay for serological diagnosis of porcine proliferative enteropathy". Veterinary Microbiology, vol. 109, 2005, pp. 105-112.

Boosinger et al., "*Campylobacter sputorum* subsp mucosalis and *Campylobacter hyointestinalis* infections in the intestine of gnotobiotic pigs". American Journal of Veterinary Research, vol. 46, No. 10, Oct. 1985, pp. 2152-2156.

Bornhorn, R., "Efficacy and economical impact of oral vaccination of partially infected piglets with Enterisol® Ileitis". Praktischer Tierarzt, vol. 88, No. 3, 2007, p. 172.

Bouma et al., "The influence of maternal immunity on the development of the in vitro lymphocyte proliferation response against pseudorabies virus in pigs". Research in Veterinary Science, vol. 64, 1998, pp. 167-171.

Brock et. al., "Immunization for Infectious Disease". Biology of Microorganisms, Ch. 16, PrenticeHall, Inc., 4th Ed., (19), 1984, pp. 557-558.

Chang et al., "*Campylobacter hyointestinalis*, a possible cause of proliferative enteritis in swine". *Campylobacter* II. Proceedings of the Second International Workshop on *Campylobacter* Infections, Brussels, Sep. 6-9, 1983, p. 131.

Chang et al., "Immunofluorescent demonstration of *Campylobacter hyointestinalis* and *Campylobacter sputorum* subsp mucosalis in swine intestines with lesions of proliferative enteritis". American Journal of Veterinary Research, vol. 45, No. 4, Apr. 1984, pp. 703-710.

Desrosiers, R., "Experiences with the Use of Enterisol® Ileitis in Canadian Breeding Animals". Ileitis Symposium, Hamburg, Germany, Jun. 28, 2004, (obtained on Jan. 6, 2009 from http://www.animal-health-online.de/drms/Vortrag_Desrosiers.pdf) pp. 1-4.

Fattom et al., "Epitopic overload at the site of injection may result in suppression of the immune response to combined capsular polysaccharide conjugate vaccines". Vaccine, vol. 17, 1999, pp. 126-133.

Finn, D.L., "Isolation and characterization of viral agents associated with porcine proliferative enteritis". A Thesis Submitted to the faculty of the Department of Microbiology and Immunology in Partial Fulfillment of the Requirements for the Degree of Master of Science with a Major in Microbiology, The University of Arizona, 1987, pp. 1-86.

Finter et al., "Large-Scale Mammalian Cell Culture: A Perspective". Large-Scale Mammalian Cell Culture, Marcel Dekker, Inc., New York and Basel, 1990, pp. 1-14.

Fox et al., "*Campylobacter*-like Omega Intracellular Antigen in Proliferative Colitis of Ferrets". Laboratory Animal Science, vol. 38, No. 1, Feb. 1988, pp. 34-36.

Frey et al., "Coiled bodies contain U7 small nuclear RNA and associate with specific DNA sequences in interphase human cells". Proceedings of the National Academy of Sciences of the United States of America, vol. 92, No. 13, Jun. 1995, pp. 5915-5919.

Gebhart et al., "Cloned DNA Probes Specific for the Intracellular *Campylobacter*-Like Organism of Porcine Proliferative Enteritis". Journal of Clinical Microbiology, vol. 29, No. 5, May 1991, pp. 1011-1015.

Gebhart et al., "Ileal Symbiont Intracellularis, an Obligate Intracellular Bacterium of Porcine Intestines Showing a Relationship to *Desulfovibrio* Species". International Journal of Systematic Bacteriology, vol. 43, No. 3, Jul. 1993, pp. 533-538.

Gebhart et al., "Species-specific DNA probes for *Campylobacter* species isolated from pigs with proliferative enteritis". Veterinary Microbiology, vol. 24, 1990, pp. 367-379.

Griffiths, B., "Scaling-up of Animal Cell Cultures". Animal Cell Culture-A Practical Approach, Chapter 3, IRL Press Limited, Oxford, England, 1986, pp. 33-69.

Guedes et al., "Validation of an immunoperoxidase monolayer assay as a serologic test for porcine proliferative enteropathy". Journal of Veterinary Diagnostic Investigation, vol. 14, 2002, pp. 528-530.

Hancock et al., Modern Microbiological Methods, Bacterial Cell Surface Techniques, A Wiley-Interscience Publication, John Wiley & Sons, Chichester, 1988, pp. 90-91.

Harvey, Stewart C., "Drug Absorption, Action and Disposition". Remington's Pharmaceutical Sciences, 18th Edition, (Ed) Gennaro AR, Mack Publishing Company, Easton, Pennsylvania, 1990, pp. 697-702.

Holyoake et al., "Enzyme-linked immunosorbent assay for measuring ileal symbiont intracellularis-specific immunoglobulin G response in sera of pigs". Journal of Clinical Microbiology, vol. 32, No. 8, 1994, pp. 1980-1985.

Horin et al., "Polymorphisms in equine immune response genes and their associations with infections". Mammalian Genome, vol. 15, 2004, pp. 843-850.

International Search Report and Written Opinion for PCT/US2007/69646 mailed on Jun. 24, 2008.

Jasni et al., "Reproduction of proliferative enteritis in hamsters with a pure culture of porcine ileal symbiont intracellularis". Veterinary Microbiology, vol. 41, 1994, pp. 1-9.

Jones et al., "Enhanced Detection of Intracellular Organism of Swine Proliferative Enteritis, Ileal Symbiont *Intracellularis*, in Feces by Polymerase Chain Reaction". Journal of Clinical Microbiology, vol. 31, No. 10, Oct. 1993, pp. 2611-2615.

Jones, Gary F., "The Diagnosis and Cause of Swine Proliferative Enteritis"., A Thesis Submitted to the Faculty of the Graduate School of the University of Minnesota, Minneapolis, MN, Jun. 1993, pp. 1-190.

Kesl et al., "Tylan® Premix and Enterisol® Li Ileitis vaccine evaluations in a *Lawsonia intracellularis* challenge model". American Swine Association of Swine Veterinarians, 2004, pp. 139-142.

Knittel et al., "Evaluation of antemortem polymerase chain reaction and serologic methods for detection of *Lawsonia intracellularis*-exposed pigs". American Journal of Veterinary Research, vol. 59, No. 6, Jun. 1998, pp. 722-723, 725.

Koyama et al., "In Vitro Cultivation and Partial Characterization of *Lawsonia intracellularis* from a Japanese Field Case of Porcine Proliferative Enteropathy". Proceedings of the 18th IPVS Congress, vol. 1, Hamburg, Germany, 2004, p. 307.

Kroll et al., "Efficacy of an Avirulent *Lawsonia intracellularis* Vaccine in Swine". Abstracts of the General Meeting of the American Society for Microbiology, vol. 101, Session No. 236/Z, Abstract Z-40, American Society for Microbiology 101st General Meeting, Orlando, FL, May 23, 2001, p. 747.

Kroll et al., "Evaluation of protective immunity in pigs following oral administration of an avirulent live vaccine of *Lawsonia intracellularis*". American Journal of Veterinary Research, vol. 65, No. 6, May 2004, pp. 559-565.

Kroll et al., "Lipopolysaccharide-Based Enzyme-Linked Immunosorbent Assay for Experimental Use in Detection of Antibodies to *Lawsonia intracellularis* in Pigs". Clinical and Diagnostic Laboratory Immunology, vol. 12, No. 6, Jun. 2005, pp. 693-699.

Kroll et al., "Maternal Immunity Associated with *Lawsonia intracellularis* Exposure and Vaccination". Proceedings of the 18th IPVS Congress, Hamburg, Germany, vol. I, 2004, p. 255.

Kuan et al., "Production of Monoclonal Antibody That Recognizes the Lipopolysaccharide of a *Campylobacter*-Like Organism". Microbiology and Immunology, vol. 36, No. 8, 1992, pp. 791-801.

Lavoie et al., "Equine proliferative enteropathy: a cause of weight loss, colic, diarrhoea and hypoproteinaemia in foals on three breeding farms in Canada". Equine Veterinary Journal, vol. 32, No. 5, Sept. 200, pp. 418-425, Abstract Only.

Lawson et al., "Attempts to Cultivate the *Campylobacter*-like Organism of the Proliferative Enteropathies". Association of Vet. Teachers and Research Workers, Apr. 1990, Abstract C50.

Lawson et al., "Infection of cultured rat enterocytes by Ileal symbiont *intracellularis* depends on host cell function and actin polymerisation". Veterinary Microbiology, vol. 45, 1995, pp. 339-350.

Lawson et al., "Intestinal Adenomatosis in the Pig: A Bacteriological Study"., Research Journal of Veterinary Sciences, vol. 37, 1974, pp. 331-336.

Lawson et al., "*Intracellular* Bacteria of Porcine Proliferative Enteropathy: Cultivation and Maintenance In Vitro". Journal of Clinical Microbiology, vol. 31, No. 5, May 1993, pp. 1136-1142.

Lawson et al., "Proliferative Haemorrhagic enteropathy". Research in Veterinary Science, vol. 27, 1979, pp. 46-51.

Lawson et al., "Review: Proliferative Enteropathy". Journal of Comparative Pathology, vol. 122, 2000, pp. 77-100.

Lomax et al., "Experimentally induced porcine proliferative enteritis in specific-pathogen-free pigs". American Journal of Veterinary Research, vol. 43, No. 9, Sep. 1982, pp. 1615-1621.

Lomax, L.G., "Porcine proliferative enteritis-characterization of the naturally occurring and experimental disease". A Dissertation Submitted to the Graduate Faculty in Partial Fulfillment of the Requirements for the Degree of Doctor of Philosophy. Iowa State Univeristy, Ames, Iowa, 1981, pp. 1-206.

\* cited by examiner

VACCINATION OF YOUNG ANIMALS AGAINST *LAWSONIA INTRACELLULARIS* INFECTIONS

RELATED APPLICATIONS

This application claims the priority benefit of U.S. Ser. No. 60/803,207, filed on May 25, 2006, the teachings and content of which are hereby incorporated by reference in their entireties.

BACKGROUND OF THE INVENTION

1. Field of the Invention

The present invention is broadly concerned with improved vaccination methods for immunization against proliferative enteritis, known as ileitis, preferably porcine proliferative ileitis, which is caused by an obligate intracellular bacterium *Lawsonia Intracellularis*. Specifically, the invention provides for a method of providing increased protection against *L. intracellularis* by vaccinating young animals starting from day one (1) of age against *L. intracellularis* infections. Preferably the young animals are vaccinated at day 1 to day 21 of age, more preferably at day 1 to day 10 of age, even more preferably at day 1 and to day 9 of age, even more preferably at day 1 to day 6 of age, even more preferably at day 1 or 2 of age, and most preferably at day 1 of age. Specifically, said young animal is a young piglet, preferably a pre-weaned piglet.

2. Description of the Prior Art

Porcine proliferative enteritis, is a naturally occurring disease that can affect pigs from weaning to young adult stage. It has been established that the causative agent is *Lawsonia Intracellularis*. *L. intracellularis* is an obligate, intracellular bacterium which cannot be cultured by normal bacteriological methods on conventional cell-free media and has been thought to require cells for growth. S. McOrist et al., Infection and Immunity, Vol. 61, No. 19, 4286-4292 (1993) and G. Lawson et al., J. of Clinical Microbiology, Vol. 31, No. 5, 1136-1142 (1993) discuss cultivation of *L. intracellularis* using IEC-18 rat intestinal epithelial cell monolayers in conventional tissue culture flasks. In U.S. Pat. Nos. 5,714,375 and 5,885,823, both of which patents are hereby incorporated by reference in their entireties, cultivation of *L. intracellularis* in suspended host cells was described.

Pathogenic and non-pathogenic attenuated bacteria strains of *L. intracellularis* are well known in the art. For example, WO 96/39629 and WO 05/011731 describe non-pathogenic attenuated strains of *L. intracellularis*. Attenuated bacteria strains of *L. intracellularis* are further described in and known from WO 02/26250 and WO 03/00665.

The disease is first characterized by its gross and microscopic pathology, and later by the demonstration of the intracellular bacteria within affected cells. The characterizing pathological feature of the disease is the proliferation of immature epithelial cells in the crypts of the ileum (terminal part of the small intestine), the large intestine or both. Sections of infected tissue are characterized by a reddened thickening mucosa resembling a "garden hose," and enteric lesions. The gut thickening ultimately prevents normal gut function, absorption capabilities, and nutrient transfer. Clinical effects of the disease are chronic weight loss, unthriftiness, diarrhea, and death. The disease is of economic importance owing to death loss, increased medication costs, poor weight gain and decreased food conversion in affected animals. Clinical cases of ileitis are observed most notably in pigs 6-20 weeks of age. However, the presence of *L. intracellularis* has been confirmed (PCR) in recently weaned pigs (3-4 weeks of age), suggesting *L. intracellularis* exposure occurs in the nursery and perhaps, originates from *Lawsonia*-positive dams (Mauch and Bilkei (2004) Vet Rec 155: 532; Marsteller et al. (2003). Swine Health Prod 11:127-130; Stege et al. (2004). Vet Micro 104: 197-206). These observations underline the importance for incorporating prevention strategies, such as vaccination earlier in the production system.

Current vaccination strategies for immunization against ileitis involve oral administration of the vaccine to *Lawsonia*-naïve pigs exclusively from three weeks of age and older, because piglets below this age group could have maternal antibodies positive for *L. intracellularis* due to previous sow exposure or vaccination. Prior to the method of the present invention it was believed that the presence of maternal antibodies or other lactogenic factors could potentially interfere with the efficacy of vaccinations in such piglets, because the maternal antibodies have the ability to neutralize the vaccine before the piglet's immune system can recognize it and begin secreting its own antibodies. Therefore, vaccination of young piglets has been avoided in the face of maternal immunity.

SUMMARY OF THE INVENTION

The present invention is based on two surprising observations. First, maternal antibodies and the sow milk do not appear effective for inactivation of *L. intracellularis* during gastrointestinal passage. The incubation of *L. intracellularis* with sow colostrum or milk did not influence the titre of a *L. intracellularis* culture over a 4 hour period of incubation at room temperature. There was no difference between samples with high or log Ig content. Even in a 1:20 dilution (5% *L. intracellularis* culture/95% milk), no effect on the titre of the culture was observed. In conclusion, no direct effect of the any of the tested sow milk samples on the titre of a *L. intracellularis* culture was detected in vitro. However, maternal immunity against *L. intracellularis* has been discussed (Holyoake, P. K. et al. (1994) J Clin Microbial 32, pp. 1980-1985; Mauch, C. H. Y. and G. Bilkei (2004) Vet. Rec. 155, 532), as young piglets usually do not suffer from Ileitis. As shown in this study, maternal antibodies and the sow milk do not appear effective for inactivation of *L. intracellularis* during gastrointestinal passage.

Second, maternal antibodies and sow milk do not interfere with *L. intracellularis* antigen, and therefore, do not prevent the establishment of active protection against *L. intracellularis* infections provided by vaccination. In fact, piglets vaccinated at day 1 of age have reduced gross pathology associated with the disease compared to non-vaccinated piglets.

Thus present invention overcomes deficiencies of the prior art and provides novel methods for providing increased protection of animals against ileitis (*L. intracellularis* infections). In particular, the present invention provides a method of vaccinating a young animal against *L. intracellularis* infections comprising the step of administering to said young animal an effective dose of *L. intracellularis* antigen. Preferably, said young animal is one (1) day of age or older. Moreover, according to another aspect, the present invention provides a method for vaccinating a young animal having or is exposed to anti-*L.intracellularis* antibodies, in particular, maternally derived anti-*L.intracellularis* antibodies, against *L intracellularis* infections, comprising the step of administering to said young animal an effective dose of *L. intracellularis* antigen. Preferably, said young animal is one (1) day of age or older.

According to another aspect, the present invention provides a method for vaccinating an animal having or is exposed to anti-*L.intracellularis* antibodies, in particular maternally derived anti-*L.intracellularis* antibodies, against *L.intracellularis* infections, comprising the step of administering to said animal an effective dose of *L. intracellularis* antigen.

The term "vaccination" or "vaccinating" as used herein means, but is not limited to, a process which includes the administration of an *L. intracellularis* antigen to an animal, wherein said *L intracellularis* antigen, when administered to said animal, elicits or is able to elicit, an immune response in said animal against *L. intracellularis*.

The term "animal" as used herein, means but is not limited to, birds, fish, and mammals, such as cattle, pigs, horses, or primates. However, according to preferred embodiment of the present invention, the animal is a pig, preferably a pre-weaned piglet.

Thus, according to a further aspect, the present invention relates to a method of vaccinating a young animal against *L. intracellularis* infection comprising the step of administering to said young animal, starting from day one (1) of age, an effective dose of *L. intracellularis* antigen, wherein said animal is a bird, fish, or mammal such as cattle, pig, horse, or primate. Preferably, said animal is a mammal. Even more preferably, said animal is a pig. Most preferably, said animal is a pre-weaned piglet.

The term "young animal" as used herein refers to an animal of 1 day of age to 20 days of age. Preferably, the term "young animal", refers to an animal of 1 day of age to 10 days of age. More preferably, the term "young animal" refers to an animal of 1 day of age to 9 days of age, even more preferably, 1 day of age to 8 days of age, even more preferably, 1 day of age to 7 days of age, even more preferably, 1 day of age to 6 days of age, even more preferably, 1 day of age to 5 days of age, even more preferably, 1 day of age to 4 days of age, even more preferably, 1 day of age to 3 days of age, even more preferably, 1 or 2 day(s) of age, and most preferably to an animal 1 day of age. The respective meaning of the term "young animal" also refers to the age of the animal when it is vaccinated for the first time with *L. intracellularis* antigen.

Thus, a further aspect of the present invention relates to a method of vaccinating a young animal against *L. intracellularis* infections, comprising the step of administering to said young animal an effective dose of *L. intracellularis* antigen, wherein the animal is vaccinated at day 1 to day 20 of age. According to a further embodiment, the present invention relates to said method of vaccination, wherein the animal is vaccinated at day 1 to day 10 of age. According to a further embodiment, the present invention relates to said method of vaccination, wherein the animal is vaccinated at day 1 to day 9 of age. According to a further embodiment, the present invention relates to said method of vaccination, wherein the animal is vaccinated at day 1 to day 8 of age.

According to a further embodiment, the present invention relates to said method of vaccination, wherein the animal is vaccinated at day 1 to day 7 of age. According to a further embodiment, the present invention relates to said method of vaccination, wherein the animal is vaccinated at day 1 to day 6 of age. According to a further embodiment, the present invention relates to said method of vaccination, wherein the animal is vaccinated at day 1 to day 5 of age. According to a further embodiment, the present invention relates to said method of vaccination, wherein the animal is vaccinated at day 1 to day 4 of age. According to a further embodiment, the present invention relates to said method of vaccination, wherein the animal is vaccinated at day 1 to day 3 of age. According to a further embodiment, the present invention relates to said method of vaccination, wherein the animal is vaccinated at day 1 or 2 of age. According to a further embodiment, the present invention relates to said method of vaccination, wherein the animal is vaccinated at day 1 of age.

The term "having or is exposed to anti-*L.intracellularis* antibodies" shall mean but is not limited to, an animal, that has or is exposed to a detectable anti-*L.intracellularis* antibody titre, preferably of at least 1:4, more preferably of more than 1:16, even more preferably of more than 1:64, even more preferably of more than 1:128, even more preferably of 1:256, even more preferably of more than 1:512, and most preferably of more than 1:1024 per ml. Preferably, that anti-*L.intracellularis* antibody titre is detectable and quantifiable in a specific anti-*L.intracellularis* immune assay, preferably in the assay as described in Example 4. More preferably, those anti-*L.intracellularis* antibodies are maternally derived antibodies.

The term "exposed to anti-*L.intracellularis* antibodies" means but is not limited to the fact that the animals are fed with a nutrients, e.g. clostrum or milk obtaining an detectable anti-*L.intracellularis* antibody titre, preferably of at least 1:4, more preferably of more than 1:16, even more preferably of more than 1:64, even more preferably of more than 1:128, even more preferably of 1:256, even more preferably of more than 1:512, and most preferably of more than 1:1024 per ml or gram nutrient.

The term "having anti-*L.intracellularis* antibodies" shall mean, but is not limited to, a detectable anti-*L.intracellularis* antibody titre in 1 ml serum of said animal, preferably of at least 1:4, even more preferably of more than 1:16, even more preferably of more than 1:64, even more preferably of more than 1:128, even more preferably of 1:256, even more preferably of more than 1:512, and most preferably of more than 1:1024.

Thus according to another aspect, the present invention provides a method for vaccinating an animal against *L.intracellularis* infection comprising the step of administering to said animal an effective dose of *L. intracellularis* antigen, wherein said animal has or is exposed to an detectable anti-*L.intracellularis* antibody titre, preferably of at least 1:4, more preferably of more than 1:16, even more preferably of more than 1:64, even more preferably of more than 1:128, even more preferably of 1:256, even more preferably of more than 1:512, and most preferably of more than 1:1024 per ml. Preferably, those antibodies are maternally derived antibodies. Even more preferably, those antibody titres are present in that animal at the day of vaccination.

Thus, according to another aspect, the present invention provides a method for vaccinating a young animal against *L.intracellularis* infections, comprising the step of administering to said young animal an effective dose of *L. intracellularis* antigen, wherein said young animal has or is exposed to a detectable anti-*L.intracellularis* antibody titre, preferably of at least 1:4, more preferably of more than 1:16, even more preferably of more than 1:64, even more preferably of more than 1:128, even more preferably of 1:256, even more preferably of more than 2:512, most preferably of more than 1:1024 per ml. Preferably, those antibodies are maternally derived antibodies. Preferably, said young animal is between 1 day of age to 20 days of age. More preferably, said young animal is between 1 day of age to 10 days of age, even more preferably, between 1 day of age to 9 days of age, even more preferably between 1 day of age to 8 days of age, even more preferably between 1 day of age to 7 days of age, even more preferably between 1 day of age to 6 days of age, even more preferably between 1 day of age to 5 days of age, even more preferably between 1 day of age to 4 days of age, even more preferably between 1 day of age to 3 days of age, even more preferably 1 or 2 day(s) of age, and most preferably 1 day of age.

The term "an effective dose" as used herein means, but is not limited to, an amount of antigen, that elicits or is able to elicit an immune response in an animal, to which said effective dose of L. intracellularis antigen is administered.

An "immunological or immune response" to a composition or vaccine is the development in the host of a cellular and/or antibody-mediated immune response to the composition or vaccine of interest. Thus, the term "elicits or is able to elicit an immune response" means, but is not limited to, an immunological process in a host characterized in that said host develops a cellular and/or antibody-mediated immune response to the composition or vaccine of interest. Usually, an "immune response" includes, but is not limited to, one or more of the following effects: the production or activation of antibodies, B cells, helper T cells, suppressor T cells, and/or cytotoxic T cells and/or yd T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction in number or severity, or lack of the symptoms associated with host infections as described herein.

The amount of antigen that is effective to elicit an immune response or is able to elicit an immune response in an animal depends on the ingredients of the vaccine and the schedule of administration. Typically, when killed bacterial antigen is used in the vaccine, the vaccine contains an amount of about $10^3$ to about $10^9$ colony forming units (CFU) of the bacterium per dose, preferably, about $10^4$ to about $10^8$ (CFU) of the bacterium per dose, and more preferably about $10^5$ to about $10^6$ (CFU) per dose.

In particular, when modified live L. intracellularis bacteria are used in vaccines, e.g. the bacteria isolates designated isolate B3903, ATCC accession No. PTA-4926 and designated isolate N34NP40wk, ATCC accession No. 55783 (both described in WO 96/39629 and WO 05/011731), the recommended dose to be administered to the susceptible animal is preferably about 3.0 $TCID_{50}$ (tissue culture infective dose 50% end point)/dose to about 6.0 $TCID_{50}$/dose and more preferably about 4.0 $TCID_{50}$/dose to about 5.0 $TCID_{50}$/dose. In a preferred embodiment, the titre of the vaccine is about 4.9 $TCID_{50}$/dose as determined by Tissue Culture Infective Dose 50% endpoint dilution assay ($TCID_{50}$). In general, the quantity of immunogen will be between 5 and 5000 micrograms, and between $10^{2.0}$ and $10^{9.0}$ $TCID_{50}$, preferably between $10^{3.0}$ and $10^{6.0}$ $TCID_{50}$, and more preferably between $10^{4.0}$ and $10^{5.0}$ $TCID_{50}$, when purified bacteria are used.

Sub-unit vaccines are normally administered with an antigen inclusion level of at least 0.2 µg antigen per dose, preferably with about 0.2 to about 400 µg/dose, still more preferably with about 0.3 to about 200 µg/dose, even more preferably 0.35 to about 100 µg/dose, still more preferably with about 0.4 to about 50 µg/dose, still more preferably with about 0.45 to about 30 µg/dose, still more preferably with about 0.6 to about 15 µg/dose, even more preferably with about 0.75 to about 8 µg/dose, even more preferably with about 1.0 to about 6 µg/dose, and still more preferably with about 1.3 to about 3.0 µg/dose.

As used herein the term "increased protection" means, but is not limited to, a statistically significant reduction of one or more clinical symptoms which are associated with L. intracellularis infections (frequency of cross lesions, etc.) in a vaccinated group of animals vs. a non-vaccinated control group of animals. The term "statistically significant reduction of clinical symptoms" means, but is not limited to, the frequency in the incidence of at least one clinical symptom in the vaccinated group of animals is at least 20%, preferably 30%, even more preferably 50%, and most preferably 70% lower than in the non-vaccinated control group after the challenge with an infectious L.intracellularis bacteria.

As used herein, the term "L. intracellularis" means the intracellular, curved gram-negative bacteria described in detail by C. Gebhart et al., Int'l. J. of Systemic Bacteriology, Vol. 43, No. 3, 533-538 (1993) and S. McOrist et al., Int'l. J. of Systemic Bacteriology, Vol. 45, No. 4, 820-825 (1995), each of which is incorporated herein by reference in their entireties, and includes, but is not limited to, the isolates described in WO 96/39629 and WO 05/011731. In particular, the term "L. intracellularis" also means, but is not limited to, the isolates deposited under the Budapest Treaty with the American Type Culture Collection, 10801 University Boulevard, Manassas, Va. 20110-2209 and assigned ATCC accession number PTA 4926 or ATCC accession number 55783. Both isolates are described in WO 96/39629 and WO 05/011731, respectively. The term "L. intracellularis" also means, but is not limited to, any other L. intracellularis bacteria strain, or isolate, preferably having the immunogenic properties of at least one of the L. intracellularis strains described in WO 96/39629 and WO 05/011731, in particular having the immunogenic properties of at least one of the isolates deposited under the Budapest Treaty with the American Type Culture Collection, 10801 University Boulevard, Manassas, Va. 20110-2209 and assigned ATCC accession numbers PTA 4926 or ATCC accession number 55783.

A strain or isolate has the "immunogenic properties" of at least one of the L. intracellularis strains described in WO 96/39629 and WO 05/011731, in particular, of the isolates deposited as ATCC accession numbers PTA 4926 or ATCC accession number 55783, when it is detectable at least with one of the anti-L. intracellularis specific antibodies, described in WO06/01294, in a detection assay that is also described in WO06/01294. Preferably those antibodies are selected from the antibodies having the reference numbers 301:39, 287:6, 268:29, 110:9, 113:2 and 268:18. Preferably, the detection assay is a sandwich ELISA as described in Examples 2 and 3 of WO06/12949, whereas antibody 110:9 is used as a capture antibody and antibody 268:29 is used as a conjugated antibody. All antibodies disclosed in WO06/12949 are produced by hybridoma cells, which are deposited at the Centre for Applied Microbiology and Research (CAMR) and European Collection of Cell Cultures (EACC), Salisbury, Wiltshire SP4 0JG, UK, as a patent deposit according to the Budapest Treaty. The date of deposit was May 11, 2004. HYBRIDOMA CELL LINE 110:9 is successfully deposited under ECACC Acc. No. 04092204. HYBRIDOMA CELL LINE 113:2 is successfully deposited under ECACC Acc. No. 04092201. HYBRIDOMA CELL LINE 268:18 is successfully deposited under ECACC Acc. No. 04092202. HYBRIDOMA CELL LINE 268:29 is successfully deposited under ECACC Acc. No. 04092206. HYBRIDOMA CELL LINE 287:6 is successfully deposited under ECACC Acc. No. 04092203. Finally, HYBRIDOMA CELL LINE 301:39 is successfully deposited under ECACC Acc. No. 04092205.

The term "*L. intracellularis* antigen" as used herein means, but is not limited to, any composition of matter, that comprises at least one antigen that can induce, stimulate or enhance the immune response against a *L. intracellularis*-caused infection when administered to an animal. Preferably, said *L. intracellularis* antigen is a complete *L. intracellularis* bacterium, in particular in an inactivated form (a so-called killed bacterium), a modified live or attenuated *L. intracellularis* bacterium (a so-called MLB), any sub-unit, polypeptide or component of *L. intracellularis*, or any chimeric vector wherein each comprises at least an immunogenic amino acid sequence of *L. intracellularis*. The terms "immunogenic protein", "immunogenic polypeptide" or "immunogenic amino acid sequence" as used herein, refer to any amino acid sequence which elicits an immune response in a host against a pathogen comprising said immunogenic protein, immunogenic polypeptide or immunogenic amino acid sequence. In particular, an "immunogenic protein", "immunogenic polypeptide" or "immunogenic amino acid sequence" of *L. intracellularis* means any amino acid sequence that codes for an antigen which elicits an immunological response against *L. intracellularis* in a host to which said "immunogenic protein", "immunogenic polypeptide" or "immunogenic amino acid sequence" is administered.

An "immunogenic protein", "immunogenic polypeptide" or "immunogenic amino acid sequence" as used herein, includes but is not limited to, the full-length sequence of any proteins, analogs thereof, or immunogenic fragments thereof. The term "immunogenic fragment" means a fragment of a protein which includes one or more epitopes and thus elicits the immunological response against the relevant pathogen. Such fragments can be identified using any number of epitope mapping techniques that are well known the art. See, e.g., Epitope Mapping Protocols in Methods in Molecular Biology, Vol. 66 (Glenn E. Morris, Ed., 1996) Humana Press, Totowa, N.J. (The teachings and content of which are incorporated by reference herein.) For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) Proc. Natl. Acad. Sci. USA 81:3998-4002; Geysen et al. (1986) Molec. Immunol. 23:709-715. (The teachings and content of which are incorporated by reference herein.) Similarly, conformational epitopes are readily identified by determining spatial conformation of amino acids such as by, e.g., x-ray crystallography and 2-dimensional nuclear magnetic resonance. See, e.g., Epitope Mapping Protocols, supra. Synthetic antigens are also included within the definition, for example, polyepitopes, flanking epitopes, and other recombinant or synthetically derived antigens. See, e.g., Bergmann et al. (1993) Eur. J. Immunol. 23:2777-2781; Bergmann et al. (1996), J. Immunol. 157:3242-3249; Suhrbier, A. (1997), Immunol. and Cell Biol. 75:402-408; Gardner et al., (1998) 12th World AIDS Conference, Geneva. Switzerland, Jun. 28-Jul. 3, 1998. (The teachings and content of which are incorporated by reference herein.)

Suitable *L. intracellularis* antigens include, but are not limited to those described in EP 1219711; U.S. Pat. No. 6,605,696; WO 96/39629; WO97/20050; WO 00/69903; WO 00/69904; WO 00/69905; WO 00/69906; WO 02/38594; WO 02/26250; WO 03/006665; WO 04/033631; WO 05/026200; and WO 05/011731.

Thus vaccine for use in accordance with the present invention includes any *L. intracellularis* antigen as described above, which elicits or is able to elicit an immune response against *L. intracellularis*. Preferably, said vaccine provides at least increased protection against *L. intracellularis*.

Thus according to a further aspect, the present invention relates to a method of vaccinating a young animal against *L. intracellularis* infections comprising the step of administering to said young animal, starting from day one (1) of age, an effective dose of *L. intracellularis* antigen, wherein the *L.intracellularis* antigen is selected from the group consisting of live modified *L. intracellularis* bacteria, killed *L. intracellularis* bacteria, or one or more sub-units of *L. intracellularis* bacteria. Preferably, the vaccine comprises modified live *L. intracellularis* bacteria. More preferably, the vaccine is Enterisol® Ileitis B3903 (Boehringer Ingelheim Vetmedica, Inc.). As mentioned above, preferably the vaccination occurs at day 1 to day 20 of age, more preferably at day 1 to day 10 of age, even more preferably at day 1 to day 9 of age, even more preferably at day 1 to day 8 of age, even more preferably at day 1 to day 7 of age, even more preferably at day 1 to day 6 of age, even more preferably at day 1 to day 5 of age, even more preferably at day 1 to day 4 of age, even more preferably at day 1 to day 3 of age, even more preferably at day 1 or 2 of age, and most preferably at day 2 of age.

According to another aspect, the present invention provides a method for vaccinating a animal against *L.intracellularis* infections, comprising the step of administering to said animal an effective dose of *L. intracellularis* antigen, wherein said animal has or is exposed to a detectable anti-*L.intracellularis* antibody titre, preferably of at least 1:4, more preferably of more than 1:16, even more preferably of more than 1:64, even more preferably of more than 1:128, even more preferably of 1:256, even more preferably of more than 1:512, and most preferably of more than 1:1024 per ml, and wherein the *L.intracellularis* antigen is selected from the group consisting of live modified *L. intracellularis* bacteria, killed *L. intracellularis* bacteria, or one or more sub-units of *L. intracellularis* bacteria. Preferably, the vaccine comprises modified live *L. intracellularis* bacteria. More preferably, the vaccine is Enterisol® Ileitis B3903 (Boehringer Ingelheim Vetmedica. Inc.). Moreover, those antibodies are preferably maternally derived antibodies. Even more preferably, those antibody titres are present in that animal at the day of vaccination.

According to another aspect, the present invention provides a method for vaccinating a young animal against *L.intracellularis* infection, comprising the step of administering to said young animal an effective dose of *L.intracellularis* antigen, wherein said young animal has or is exposed to a detectable anti-*L.intracellularis* antibody titre, preferably of at least 1:4, more preferably of more than 1:16, even more preferably of more than 1:64, even more preferably of more than 1:128, even more preferably of 1:256, even more preferably of more than 1:512, most preferably of more than 1:1024 per ml, and wherein the *L.intracellularis* antigen is selected from the group consisting of live modified *L. intracellularis* bacteria, killed *L. intracellularis* bacteria or one or more sub-units of *L. intracellularis* bacteria. Preferably, the vaccine comprises modified live *L. intracellularis* bacteria. More preferably, the vaccine is Enterisol® Ileitis B3903 (Boehringer Ingelheim Vetmedica, Inc.). Moreover, those antibodies are preferably maternally derived antibodies. Even more preferably, those antibody titres are present in that animal at the day of vaccination. Preferably, said young animal is between 1 day of age to 20 days of age. More preferably, said young is between 1 day of age to 10 days of age, even more preferably, between 1 day of age to 9 days of age, even more preferably between 1 day of age to 8 days of age, even more preferably between 1 day of age to 7 days of age, even more preferably between 1 day of age to 6 days of age, even more preferably between 1 day of age to 5 days of age, even more preferably between 1 day of age to 4 days of age, even more preferably between 1 day of age to 3 days of age, even more preferably 1 or 2 day(s) of age, and most preferably 1 day of age.

According to a further aspect, the present invention relates to a method of vaccinating a young animal against *L. intracellularis* infections comprising the step administering to said young animal starting from day one (1) of age a dose of about 3.0 $TCID_{50}$ to about 6.0 $TCID_{50}$ of the live modified *L. intracellularis* bacteria. Preferably, said bacteria is that included in the vaccine Enterisol® Ileitis B3903 (Boehringer Ingelheim Vetmedica, Inc.). As mentioned above, preferably the vaccination occurs at day 1 to day 20 of age, more preferably at day 1 to day 10 of age, even more preferably at day 1 to day 9 of age, even more preferably at day 1 to day 8 of age, even more preferably at day 1 to day 7 of age, even more preferably at day 1 to day 6 of age, even more preferably at day 1 to day 5 of age, even more preferably at day 1 to day 4 of age, even more preferably at day 1 to day 3 of age, even more preferably at day 1 or 2 of age, and most preferably at day 1 of age.

According to a further aspect, the present invention relates to a method of vaccinating an animal against *L. intracellularis* infection, comprising the step of administering to said animal a dose of about 3.0 $TCID_{50}$ to about 6.0 $TCID_{50}$ of the live modified *L. intracellularis* bacteria, wherein said animal has or is exposed to a detectable anti-*L.intracellularis* antibody titre, preferably of at least 1:4, more preferably of more than 1:16, even more preferably of more than 1:64, even more preferably of more than 1:128, even more preferably of 1:256, even more preferably of more than 1:512, and most preferably of more than 1:1024 per ml. Preferably, said bacteria is that included in the vaccine Enterisol® Ileitis B3903 (Boehringer Ingelheim Vetmedica, Inc.).

According to a further aspect, the present invention relates to a method of vaccinating a young animal against *L. intracellularis* infections comprising the step of administering to said young animal a dose of about 3.0 $TCID_{50}$ to about 6.0 $TCID_{50}$ of the live modified *L. intracellularis* bacteria, wherein said young animal has or is exposed to a detectable anti-*L.intracellularis* antibody titre, preferably of at least 1:4, more preferably of more than 1:16, even more preferably of more than 1:64, even more preferably of more than 1:128, even more preferably of 1:256, even more preferably of more than 1:512, and most preferably of more than 1:1024 per ml. Preferably, said bacteria is that included in the vaccine Enterisol® Ileitis B3903 (Boehringer Ingelheim Vetmedica, Inc.). As mentioned above, preferably the vaccination occurs at day 1 to day 20 of age, more preferably at day 1 to day 10 of age, even more preferably at day 1 to day 9 of age, even more preferably at day 1 to day 8 of age, even more preferably at day 1 to day 7 of age, even more preferably at day 1 to day 6 of age, even more preferably at day 1 to day 5 of age, even more preferably at day 1 to day 4 of age, even more preferably at day 2 to day 3 of age, even more preferably at day 1 or 2 of age, and most preferably at day 1 of age.

According to a further aspect, the present invention relates to a method of vaccinating a young animal against *L. intracellularis* infection, comprising the step of administering to said young animal, starting from day one (1) of age, an effective dose of *L. intracellularis* antigen, wherein the young animal is *L. intracellularis* and anti-*L. intracellularis* maternal antibody negative. As mentioned above, preferably the vaccination occurs at day 1 to day 20 of age, more preferably at day 1 to day 10 of age, even more preferably at day 1 to day 9 of age, even more preferably at day 1 to day 8 of age, even more preferably at day 1 to day 7 of age, even more preferably at day 1 to day 6 of age, even more preferably at day 1 to day 5 of age, even more preferably at day 1 to day 4 of age, even more preferably at day 1 to day 3 of age, even more preferably at day 1 or 2 of age, and most preferably at day 1 of age.

According to a further aspect, the present invention also relates to a new medicinal use of an *L. intracellularis* antigen for the preparation of medicament, preferably a vaccine composition, for the vaccination of a young animal starting at day one (1) of age against *L. intracellularis* infections, wherein said young animal is vaccinated at day one (1) of age or older with an effective dose of said *L. intracellularis* antigen. Preferably, the vaccination occurs at day 1 to day 20 of age, more preferably at day 1 to day 10 of age, even more preferably at day 1 to day 9 of age, even more preferably at day 1 to day 8 of age, even more preferably at day 1 to day 7 of age, even more preferably at day 1 to day 6 of age, even more preferably at day 1 to day 5 of age, even more preferably at day 1 to day 4 of age, even more preferably at day 1 to day 3 of age, even more preferably at day 1 or 2 of age, and most preferably at day 1 of age.

According to a further aspect, the present invention also relates to a new medicinal use of an *L. intracellularis* antigen for the preparation of medicament, preferably a vaccine composition, for the vaccination of an animal against *L. intracellularis* infection, wherein said animal has or is exposed to a detectable anti-*L.intracellularis* antibody titre, preferably of at least 1:4, more preferably of more than 1:16, even more preferably of more than 1:64, even more preferably of more than 1:128, even more preferably of 1:256 even more preferably of more than 1:512, and most preferably of more than 1:1024 per ml.

According to a further aspect, the present invention also relates to a new medicinal use of an *L. intracellularis* antigen for the preparation of medicament, preferably a vaccine composition, for the vaccination of a young animal against *L. intracellularis* infection, wherein said young animal has or is exposed to a detectable anti-*L.intracellularis* antibody titre, preferably of at least 1:4, more preferably of more than 1:16, even more preferably of more than 1:64, even more preferably of more than 1:128, even more preferably of 1:256, even more preferably of more than 1:512, and most preferably of more than 1:1024 per ml. Preferably, the vaccination occurs at day 1 to day 20 of age, more preferably at day 1 to day 10 of age, even more preferably at day 1 to day 9 of age, even more preferably at day 1 to day 8 of age, even more preferably at day 1 to day 7 of age, even more preferably at day 1 to day 6 of age, even more preferably at day 1 to day 5 of age, even more preferably at day 1 to day 4 of age, even more preferably at day 1 to day 3 of age, even more preferably at day 1 or 2 of age, and most preferably at day 1 of age.

According to a further aspect of said medicinal uses described above, the *L. intracellularis* antigen is selected from the group consisting of live modified *L. intracellularis* bacteria, killed *L. intracellularis* bacteria or one or more sub-units of *L.intracellularis* bacteria. Preferably, the *L. intracellularis* antigen is live modified *L. intracellularis* bacteria. More preferably, said animals are administered with a dose of about 3.0 $TCID_{50}$ to about 6.0 $TCID_{50}$ of the live modified *L. intracellularis* bacteria.

The manufacture of vaccine compositions comprising a *L. intracellularis* antigen are state of the art and known to a skilled artisan. For example, the skilled person in the art is able to determine additional components which may be comprised in said composition (see also Remington's Pharmaceutical Sciences. (1990). 18th ed. Mack Publ., Easton). The expert may use known injectable, physiologically acceptable sterile solutions. For preparing a ready-to-use solution for parenteral injection injection or infusion, aqueous isotonic solutions, such as e.g. saline or corresponding plasma protein solutions, are readily available. The vaccine compositions may be present as lyophylisates or dry preparations, which can be reconstituted with a known injectable solution directly before use under sterile conditions, e.g. as a kit of parts.

In addition, the immunogenic and vaccine compositions of the present invention can include one or more veterinary-acceptable carriers. As used herein, "a veterinary-acceptable carrier" includes any and all solvents, dispersion media, coatings, adjuvants, stabilizing agents, diluents, preservatives, antibacterial and antifungal agents, isotonic agents, adsorption delaying agents, and the like.

"Diluents" can include water, saline, dextrose, ethanol, glycerol, and the like. Isotonic agents can include sodium chloride, dextrose, mannitol, sorbitol, and lactose, among others. Stabilizers include albumin and alkalisalts of ethylendiamintetracetic acid, among others.

"Adjuvants" as used herein, can include aluminum hydroxide and aluminum phosphate, saponins e.g., Quil A, QS-21 (Cambridge Biotech Inc., Cambridge Mass.), GPI-0100 (Galencia Pharmaceuticals, Inc. Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; and esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, or polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.). John Wiley and Sons, NY, pp 51-94 (1995)and Todd et al., Vaccine 15:564-570 (1997). (The teachings and content of which are hereby incorporated by reference.)

For example, it is possible to use the SPT emulsion described on page 147 "Vaccine Design, The Subunit and Adjuvant Approach" edited by M. Powell and M. Newman, Plenum Press, 1995, and the emulsion MF59 described on page 183 of this same book. (The teachings and content of which are hereby incorporated by reference.)

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 3, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol (BF Goodrich, Ohio, USA) are particularly appropriate. They are cross-linked with an allyl sucrose or with allyl pentaerythritol. Among them, there may be mentioned Carbopol 974P, 934P and 971P. Most preferred is the use of Cabopol 971P. Among the copolymers of maleic anhydride and alkenyl derivative, is the copolymer EMA (Monsanto), which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from *E. coli* (recombinant or otherwise), cholera toxin, IMS 1314 or muramyl dipeptide among many others.

Preferably, the adjuvant is added in an amount of about 100 µg to about 10 mg per dose. Even more preferably, the adjuvant is added in an amount of about 100 µg to about 10 mg per dose. Even more preferably, the adjuvant is added in an amount of about 500 µg to about 5 mg per dose. Even more preferably, the adjuvant is added in an amount of about 750 µg to about 2.5 mg per dose. Most preferably, the adjuvant is added in an amount of about 1 mg per dose.

The vaccine composition can further include one or more other immunomodulatory agents such as, e. g., interleukins, interferons, or other cytokines. The vaccine compositions can also include Gentamicin and Merthiolate. While the amounts and concentrations of adjuvants and additives useful in the context of the present invention can readily be determined by the skilled artisan, the present invention contemplates compositions comprising from about 50 ug to about 2000 ug of adjuvant and preferably about 250 ug/ml dose of the vaccine composition. In another preferred embodiment, the present invention contemplates vaccine compositions comprising from about 1 ug/ml to about 60 ug/ml of antibiotics, and more preferably less than about 30 ug/ml of antibiotics.

The vaccine is administered to animals, preferably mammals, and still more preferably pigs, in any conventional manner, most preferably through oral drench. The dosage to be administered will depend upon the particular case, but in any event, it is the amount sufficient to induce a protective antibody or cell-mediated immune response against ileitis.

The vaccines according to the invention are generally administered to susceptible animals, preferably to young piglets and/or piglets having anti-*L.intracellularis* antibodies or being exposed to anti-*L.intracellularis* antibodies in one or more doses. Live or killed vaccine may be administered 1 or 2 times at 2 to 4 week intervals after the initial vaccination. For the attenuated, live vaccines, one dose is preferred. preferably, the first or single administration is performed at day 1 to day 20 of age, more preferably at day 1 to day 10 of age, even more preferably at day 1 to day 9 of age, even more preferably at day 1 to day 8 of age, even more preferably at day 1 to day 7 of age, even more preferably at day 1 to day 6 of age, even more preferably at day 1 to day 5 of age, even more preferably at day 1 to day 4 of age, even more preferably at day 1 to day 3 of age, even more preferably at day 1 or 2 of age, and most preferably at day 1 of age, as described above.

If a second administration is desirable or necessary, the second administration is performed about 1 to about 4 weeks after the first administration of the vaccine. According to a further aspect, revaccination is performed in an interval of 3 to 12 months after administration of any previous vaccination. Administration of subsequent vaccine doses is preferably done on a 6 month to an annual basis. In another preferred aspect, animals vaccinated before the age of about 2 to 3 weeks should be revaccinated. Administration of subsequent vaccine doses is preferably done on an annual basis.

The present invention is further described in the following examples which are provided for illustrative purposes only and are not to be construed as limiting. Indeed, other variants of the invention will be readily apparent to one of ordinary skill in the art.

All publications and patents cited herein are incorporated by reference in their entireties.

EXAMPLES

Example 1

Detection of Antibodies Specific to L. intracellularis in Colostrum and Milk Samples from Sows (>1 Litter) and Gilts (1$^{st}$ Litter)

Material and Methods

Colostrum samples were taken from 25 sows and 25 gilts within 24 hours after farrowing. Milk samples were taken in the first and second week of lactation from the same pigs. Samples were centrifuged twice with 200 g for 10 minutes at 4° C. to separate the fatty portion of the milk. The watery portion of the samples was stored at −20° C. until analysis. Specific antibodies against L. intracellularis were detected in serial 2 fold dilutions starting with an initial dilution of 1:20 in an IFAT. The IFAT was performed as described in Example 5 and elsewhere, with the exception that for each sample, FITC-labelled anti-swine IgG, IgM, and IgA antibodies were used to detect the different classes of Ig. Parallel blood samples from the sows and gilts were taken with 24 hours after farrowing. These samples were examined in the Enterisol® Ileitis ELISA according to the instructions of the manufacturer.

Results

Figure 1:
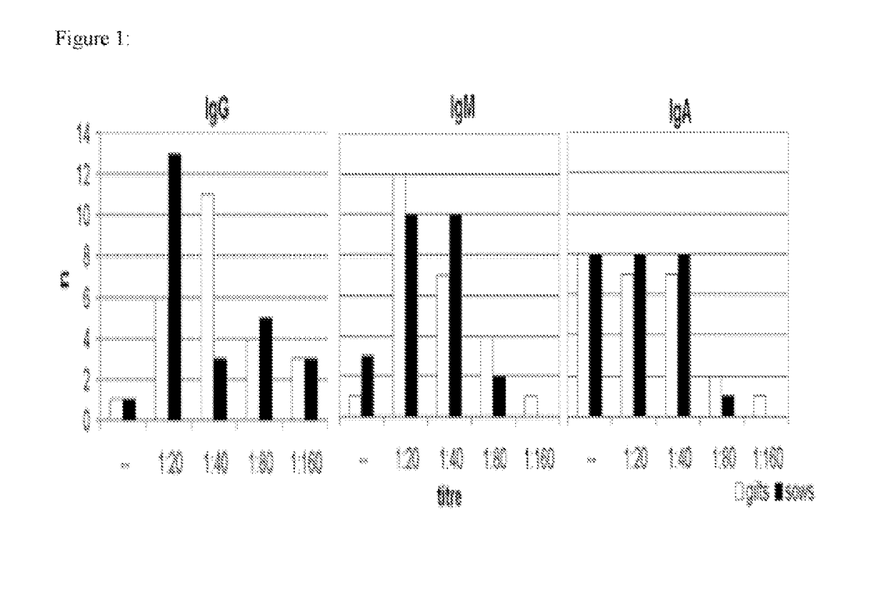
FIG. 1 shows the number of colostrum samples positive in the IFAT for IgG, IgM and IgA.
Figure 2:
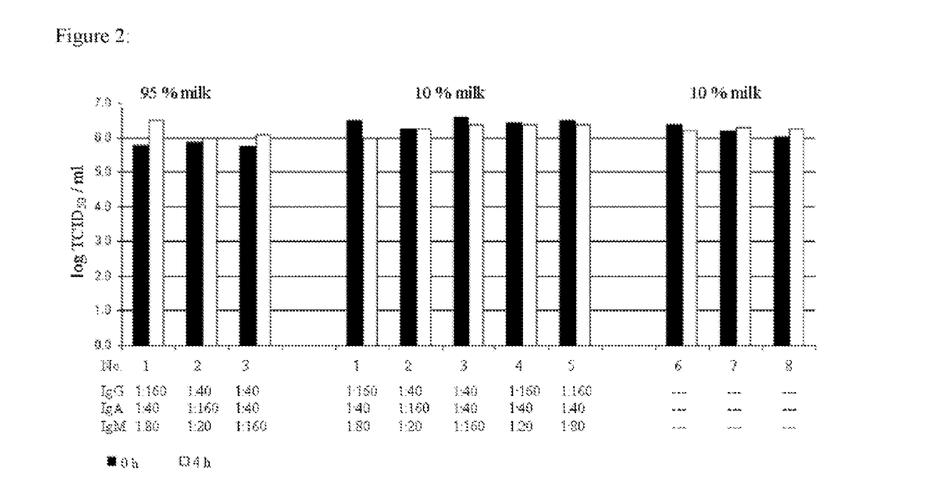
FIG. 2 shows the titre of *L. intracellularis* culture (mean of two titrations) in sow milk samples with different Ig content.

The results of the antibody detection in colostrum samples are summarized in FIG. 1. The figure shows the number of samples scoring positive results for IgG, IgM and IgA of different dilutions in the IFAT. None of the colostrum samples were negative in all examinations. Only one of the colostrum samples from sows and one from gilts was negative for IgG, whereas in one sample from gilts and in three samples from sows, no specific IgM's were detectable. Eight (8) out of twenty-five (25) samples obtained from gilts and sows, respectively, scored negative for IgA specific to L. intracellularis. In the milk samples, obtained at the 2$^{nd}$ week of lactation, only two samples from sows scored a titre of 1:20 for IgG, whereas one sample from a gilt scored positive for IgA (1:20). At the 3$^{rd}$ week of lactation the samples from one sow and three gilts scored positive results for IgG at a dilution of 1:20. All other samples from the 2$^{nd}$ and 3$^{rd}$ week of lactation tested negative for IgG, IgM and IgA. All blood samples taken from sows within 24 h after farrowing were positive in the Enterisol® Ileitis ELISA, whereas two out of twenty-five samples obtained from gilts scored negative results. There was no obvious correlation between the results from the blood samples and the results from the colostrum samples. It can be concluded that in colostrum from sows and gilts, antibodies of the Ig classes G, M and A, specific to L. intracellularis, are present. However in milk samples taken one week after farrowing, only low titres of L. intracellularis specific antibodies could be detected in only 6% of the samples.

References
1. McOrist, S. et al. (2003) Pig J. 51, 26-35
2. Collins, A. M. et al. (2001) Allen D. Leman Swine, Conference
3. Holyoake, P. K. et al. (1994) J Clin Microbiol 32, 1980-1985, Kruse, P. E. (1983) Ann. Rech. Vet. 14, 349-353
4. Bollwein, J. (2004) Doctoral thesis, LMU, Munich
5. Knittel J. P. et al. (1998) AJVR 59, 722-726.

Example 2

Direct Impact of Milk Antibodies on L. intracellularis During Gastro-intestinal Passage Material and Methods Colostrum samples were taken from sows and gilts within 24 hours after birth. Sow milk samples were taken in the first and second week of lactation. Samples were centrifuged twice with 2000 g for 10 minutes at 4° C. to separate the fatty portion of the milk. The watery portion of the samples was stored at −20° C. until analysis. Specific antibodies against L. intracellularis were detected in serial 2 fold dilutions starting with an initial dilution of 1:20 in an IFAT. The IFAT was performed as described in Example 5 and elsewhere (5), with the exception that for each sample, FITC-labelled anti-swine IgG, IgM and IgA, antibodies were used to detect the different classes of Ig. Milk samples with different content of Ig were selected on basis of IFAT results. A L. intracellularis culture was incubated with different dilutions in colostrum or sow milk samples at room temperature. Each sample was tested twice. The tissue culture infectious dose (TCID$_{50}$) of L. intracellularis was measured at the beginning (0 hours) and after 4 hours incubation at room temperature. An undiluted sample of the culture served as a control for the test performance. For each determination of the TCID$_{50}$ value, the sample was homogenized by 20 passages through a 20 gauge needle. Cells from one 75 cm$^2$ tissue culture flask with a 100% confluent monolayer of McCoy cells, grown with DMEM/HAM's F12 medium, were trypsinated and divided on four 96-well microtitre plates. Serial dilution from $10^{-1}$ to $10^{-7}$ of the samples were inoculated six times each on the fresh McCoy cells. After an incubation of 6 days at 37° C. under microaerophilic conditions, cells were fixed by ice cold acetone/methanol (50:50, v/v). Growth of L. intracellularis was detected by the use of a specific monoclonal anti-Lawsonia antibody and subsequent labelling by an FITC-labelled anti-mouse antibody. Each well containing one or more McCoy cells with 5 or more fluorescent L. intracellularis was judged as positive. TCID$_{50}$ was determined by the use of the 50% endpoint formula according to Spearmann and Karber (6).

Results

In FIG. 1 the results from the TCID$_{50}$ tests and the IgG, IgA and IgM titres of 8 colostrum (No. 1-5) and milk (No. 6-8) samples are summarized. The control sample of the culture scored, in all experiments, the expected TCID$_{50}$ value. In none of the tests the titre of the L. intracellularis changed substantially during the 4 hour incubation at room temperature. Thus, as shown in this study, maternal antibodies and the sow milk seem not to be effective in inactivation of *L. intracellularis* during gastrointestinal passage.

References 1. van Aken; N. et al. (2002) Proc. 17$^{th}$ IPVS, Ames, Iowa, USA
2. Kruse, P. E. (1983) Ann. Rech. Vet. 14, 349-353
3. Collins, A. M. et al. (2001) Allen D. Leman Swine, Conference
4. Holyoake, P. K. et al. (1994) J Clin Microbiol 32, pp. 1980-1985
5. Knittel, J. P. et al. (1998) AJVR 59, 722-726.
6. Karber, G. (1931) Arch. exp. Path. Pharma. 162, 480
7. Mauch, C. H. Y. and G. Bilkei (2004) Vet. Rec. 155, 532

Example 3

Efficacy of Vaccination of Piglets of One Day of Age Against *L. intracellularis* Infections Materials and Methods The study consisted of three experimental groups involving *L. intracellularis* negative and anti-*Lawsonia* maternal antibody negative suckling piglets at 1 day of age. On day 0 of the study, 20 piglets each in group 1 (vaccinates) received an oral dose of Enterisol® Ileitis, vaccine isolate B3903, per label instructions (3). Twenty piglets in group 2 (controls) received a placebo consisting of growth medium. Piglets in all groups were weaned on day 20 of the study. On day 21, piglets in groups 1 and 2 received an intestinal homogenate containing 3.5×10$^9$ of virulent *L. intracellularis* 2688/2685 via gavage. A third group of 10 pigs (strict controls) did not receive vaccine, placebo or challenge at any time period throughout the study. On day 42, pigs in all groups were humanely euthanized and necropsied. Primary efficacy parameters included gross and microscopic lesions of the ileum, caecum and colon specifically caused by *L. intracellularis*. Secondary parameters included clinical health (behaviour, body condition, and stool consistency), average daily weight gains, faecal shedding (PCR), and seroconversion (IFAT) (1).

Results

At necropsy (day 42), vaccinates (group 2) had significantly ($p<0.0003$) less average gross lesion scores in the ileum (0.21), caecum (0.0) and colon (0.0) compared to non-vaccinated, control pigs (ileum=1.16, caecum=0.42, and colon=0.16). Average total intestinal lesion length (ileum, caecum and colon) was significantly ($p-0.0001$) higher in the controls (8.89 cm) compared to vaccinated pigs (1.42 cm). Group 3 (strict controls) had an average gross intestinal lesion score of 0.22 and were considered normal.

*Lawsonia*-specific average microscopic lesion scores in the ileum were significantly ($p<0.02$) higher in the controls (2.47) compared to vaccinated pigs (0.53). Additionally, the total microscopic lesion score ($p<0.006$) and percentage of IHC positive pigs ($p<0.0001$) was significantly higher in the controls compared to the vaccinated group. The control group had nominally higher mean microscopic lesion scores and percent IHC positive animals than the vaccinate group in the caecum and colon ($p>0.05$). Significantly ($p<0.05$) more control pigs were PCR positive 2 weeks after challenge (day 35) than the vaccinate group. Pigs in the control group (8/19) shed nominally more *L. intracellularis* than those in the vaccinated group (3/19) on the last day of the study (day 42, $p>0.05$). There was no significant ($p>0.05$) difference in average daily weight gains or average clinical scores between groups 1 and 2 during the study. Altogether, the primary efficacy parameters (gross and microscopic intestinal lesion development) demonstrated that a single oral dose of Enterisol® Ileitis is efficacious against a virulent challenge when administered to maternal antibody negative, *Lawsonia*-naïve piglets at 1 day of age. Non-*Lawsonia* specific lactogenic properties potentially present in the colostrum and milk during the suckling period did not interfere or prevent vaccine efficacy against virulent *L. intracellularis* challenge exposure in this study.

TABLE 1

Rates of *L. intracellularis* faecal shedding.

| Group | *Group ID | Days 0 to 21 PCR positive | Day 28 PCR positive | Day 35 PCR positive | Day 42 PCR positive |
|---|---|---|---|---|---|
| 1 | Vaccinates | 0/19$^a$ | 0/19$^a$ | 0/19$^a$ | 3/19$^a$ |
| 2 | Challenge Controls | 1/19$^a$ | 0/19$^a$ | 5/19$^b$ | 8/19$^a$ |
| 3 | $^\Phi$Strict Controls | 1/9 | 0/9 | 0/9 | 0/9 |

$^{a,b}$Like letters indicate no significant difference ($p < 0.05$)
$^\Phi$Strict controls were not statistically analyzed
*One pig was removed from each group due to poor health unrelated to *L. intracellularis*

References

1. McOrist et al. (1993) Infection and Immunity 61: 4286-4292.
2. Knittel et al. (1998) Am J Vet Res 59:722-726.
3. Kroll et al. (2004) Am J Vet Res 65:559-565
4. Mauch and Bilkei (2004) Vet Rec 155: 532
5. Marsteller et al. (2003). Swine Health Prod 11:127-130
6. Stege et al. (2004). Vet Micro 104: 197-206

Example 4

IFAT for Detection and Quantification of Anti-*L. intracellularis* Antibodies

Material and Methods:

Prior to study initiation, 16 healthy, pregnant and *L. intracellularis* negative sows were randomly allocated into 2 groups; 8 hyperimmunized (Group A) and 8 placebo-administered controls (Group B). On Days −55, −35 and −14 prior to farrowing, each sow in Group A was hyperimmunized with commercially available Enterisol® Ileitis by direct oral drench. The administration of the vaccine dose by this method involved applying the vaccine to the posterior portion of the oral cavity using a sterile, plastic 10 ml syringe. The control group (Group B) received an equivalent dose of placebo consisting of uninfected McCoy cells suspended in growth medium. Hyperimmunization of pregnant sows in Group A was performed in an attempt to induce a high level of maternal immunity prior to farrowing. Each pregnant sow group was housed in separate rooms, to avoid cross contamination, and under the same conditions (temperature, ventilation, and pen size). Sows in each room were kept in the same pen.

Although efforts were made by the study investigator to have uniform conception and farrowing dates, sows did not all farrow on the same day. Instead, farrowing occurred during a 10-day period. To prevent having multiple vaccination and challenge dates which could lead to excessive variability among pig groups in the study, the mean date of farrow during the farrowing period was established as Day 0 of the study. Thus, pigs were 3 weeks±5 days of age at the time of vaccination (Day 21).

On Day 21, one hundred healthy, weaned piglets were sorted by litter and randomly assigned to six treatment groups. Housing restrictions and conditions were similar to the sow groups mentioned above. Piglets derived from hyperimmunized sows (Group A) were randomly assigned to Groups 1 through 3 and were identified as "hyperimmune-derived" piglets for the remainder of the study. Piglets derived from control sows (Group B) were randomly assigned to Groups 4 through 6 and were identified as "placebo-derived" piglets for the remainder of the study. Groups 1 and 4 (20 pigs/group, respectively) were given a single 2 ml dose of Enterisol® Ileitis by direct oral drench. Groups 2 and 5 (20 pigs/group, respectively) were given an equivalent dose of placebo (uninfected McCoy cells+media). Groups 3 and 6 (10 pigs/group) were designated "strict negative controls" which did not receive a vaccine or placebo treatment and were not challenge exposed during this study. On Day 22, after the weaning period, sows were humanely euthanized and necropsied for evaluations of intestinal lesion development due to PE.

On Day 42 of the study, Groups 1, 2, 4 and 5 received $1 \times 10^{7.3}$ TCID$_{50}$/dose of heterologous virulent pure culture *L. intracellularis* isolate N101494 via intragastric gavage. All piglets were examined daily 21-days post challenge for clinical symptoms related to PE; diarrhoea, behavior and body condition and were given a score of 1 to 4 dependent on severity (1=clinically normal; 4=severe illness). Pigs were weighed on Days 21, 42 and 63 of the study to calculate an average daily weight gain per pig group. Average daily weight gains (ADWG) were calculated to analyze the effects of treatment in relation to normal growth performance in pigs. Pigs were initially weighed to obtain a baseline average group weight prior to receiving a vaccine or placebo treatment. All groups were found to be uniform in size (variation of <0.63 kg/pig). The first key ADWG evaluation period among groups occurred from Day 21 (vaccination) to Day 42 (challenge exposure) to measure the immediate effects of vaccination or placebo inoculation. The second evaluation period was from Day 42 to 63 (necropsy) to measure the effects of challenge exposure with a virulent pure culture *L. intracellularis*.

On Day 63 of the study, all pigs were humanely euthanized and necropsied for evaluations of intestinal lesion development due to PE.

Results

Maternal Antibody Detection

*Lawsonia intracellularis*-specific IgG, IgA and IgM antibodies were detected in the sera and colostrum of sows in Group A (hyperimmunized) during the farrowing period. Sixty three percent (5/8 sows) of Group A sows were serum antibody positive for anti-*Lawsonia* IgG antibodies while 0% (0/8) of the sows in Group B (control) were positive at farrowing. In addition, serum IgG antibodies were detected in piglets derived from Group A sows only from farrowing (Day 0) to 5 weeks of age (Day 28), see FIG. 1. Anti-*Lawsonia* IgG, IgA and IgM were detected in the colostrum of Group A sows at 50%, 75% and 12.5% respectively. Average antibody concentrations in the colostrum of Group A sows were 1:14 (IgG, range=1 to 1:64), 1:10 (IgA, range=1 to 1:32), and 1.4 (IgM, range 1 to 1:4). Sows in Group B did not have any detectable IgM or IgG anti-*Lawsonia* antibodies in their colostrum during this time period. One pig in sow Group B was positive for IgA at a titre of 1:16.

Maternal Protection

The comparison of unvaccinated, control pigs in Group 2 (pigs derived from sow Group A) to Group 5 (pigs from sow Group B) was conducted to evaluate the potential of maternal protection against virulent *L. intracellularis* exposure derived from sows hyperimmunized with vaccine (Group A sows).

Average gross and microscopic lesion scores among all groups are summarized in Table 1. Pigs in Group 5 (77%) had a higher percentage of *Lawsonia*-specific lesions in the ileum and colon than Group 2 pigs (27.5%). Group 2 pigs had significantly ($p<0.05$) lower average gross lesion scores in the ileum and average microscopic (IHC) lesion scores in the ileum and colon compared to Group 5 at Day 63 of the study.

No detectable shedding of *L. intracellularis* in the faeces, by PCR, was evident in either group on Days 21 (vaccination) to 42 (challenge) of the study, see FIG. 3. Groups 2 and 5 were initially faecal PCR positive beginning on Day 49 and remained positive until Day 63 (study termination) with 5% to 25% and 15% to 72%, respectively, of the pigs shedding *L. intracellularis* during this time period. Significantly ($p<0.05$) less faecal shedding was detected by PCR in Group 2 (25%) compared to Group 5 (72%) on Day 63 of the study.

A higher percentage of tissue PCR positives were found in the ilea of pigs in Group 5 (45%) compared to Group 2 (25%) at Day 63 of the study. Pigs in Group 2 were PCR negative for *L. intracellularis* in the tonsil, mesenteric lymph node and colon. Various PCR positives were observed in the colon and mesenteric lymph tissue of Group 5 pigs as mentioned in Section 3.4 above.

Average weight gain comparisons among all test groups are summarized in Table 2. Average initial weights were uniform among Groups 2 and 5 on Day 21 (vaccination) with pigs weighing 6.35 and 6.10 kg/pig respectively. No significant difference in ADWG was found among Groups 2 (0.40 kg/pig) and 5 (0.41 kg/pig) from Day 21 (vaccination) to Day 42 (challenge). However, significantly ($p<0.05$) higher ADWG was evident in Group 2 pigs (0.46 kg/pig) than Group 5 pigs (0.40 kg/pig) during the 21-day evaluation period from Day 21 (challenge) to Day 63 (study termination) of the study.

Vaccine Efficacy in Hyperimmune-Derived Pigs

The comparison of pigs vaccinated with Enterisol® Ileitis in Group 1 to unvaccinated, control pigs in Group 2 was conducted to confirm that vaccination in the face of maternal immunity could be accomplished by evaluating protective immunity against PE after vaccination of pigs at 3 weeks of age. Both groups of pigs were derived from sows' hyperimmunized with vaccine (Group A sows). Furthermore, primary and secondary efficacy parameters were analyzed between vaccine-treated pigs to Group 1 and Group 4 to determine if vaccine efficacy is similar against virulent *L. intracellularis* challenge.

Average gross and microscopic lesion scores among all groups are summarized in Table 1. Pigs in Group 2 (27.5%) had a higher percentage of *Lawsonia*-specific lesions in the ileum and colon than Group 1 (12.5%). Group 1 pigs had significantly ($p<0.05$) lower average gross lesion scores (ileum) and numerically lower average microscopic (IHC) lesion scores (ileum and colon) compared to Group 2 at Day 63 of the study. In addition, there were no significant differences among average gross and microscopic lesion scores or lesion severity in pigs receiving a vaccination (Groups 1 and 4).

No detectable shedding of *L. intracellularis* in the faeces by PCR was evident in either group (1 or 2) on Days 21 (vaccination) to 35 of the study, see FIG. 3. Group 1 pigs were initially faecal PCR positive on Day 42 (challenge) and remained positive until Day 63 (study termination) with 11% to 16% of the pigs shedding *L. intracellularis* during this time period. Pigs in Group 2 were initially faecal PCR positive on Day 49 and remained positive until Day 63 (study termination) with 5% to 25% of the pigs shedding *L. intracellularis* during this time period. Pigs in Group 4 were not PCR positive for *Lawsonia* DNA until Day 42 (challenge) and remained positive until Day 63 (study termination) with decreasing rates of shedding from 25% to 5%. No evidence of a significant difference in the rates of faecal shedding of *L. intracellularis* between Groups 1 and 2 and Groups 1 and 4 during the study.

A slightly higher percentage of tissue PCR positives were found in the ilea of pigs in Group 2 (25%) compared to Group 1 (20%) at Day 63 (study termination) of the study. A lower frequency of tissue PCR positives was evident in Group 4 (5%) than Groups 1 and 2 at study termination. No significant differences in PCR positives were noted among Groups 1 and 2 and Groups 1 and 4 respectively. Pigs in all three groups were PCR negative for *L. intracellularis* in the tonsil, mesenteric lymph node, and colon.

Average weight gain comparisons among all test groups are summarized in Table 2. Average initial weights were uniform among Groups 1 and 2 on Day 21 (vaccination) with pigs weighing 6.53 and 6.35 kg/pig respectively. Uniform average weights were also observed among Groups 1 and 4 on Day 21 (6.53 kg/pig and 6.44 kg/pig, respectively). No significant difference in ADWG among Groups 1 (0.40 kg/pig) and 2 (0.41 kg/pig) or among Groups 1 and 4 (0.44 kg/pig) from Day 21 (vaccination) to Day 42 (challenge). Significant differences ($p<0.05$) in ADWG were evident in Group 1 pigs (0.45 kg/pig) compared to Group 4 pigs (0.51 kg/pig) during the 21-day evaluation period from Day 21 (challenge) to Day 63 (study termination). No significant differences in ADWG among Groups 1 and 2 were noted from Day 21 to Day 63 in this study.

Example 5

IFAT for Detection and Quantification of Anti-*L. intracellularis* Antibodies

Serum samples from the blood of each sow and pig were tested for the presence of IgG antibodies against *L. intracellularis* by the Immunofluorescence antibody test (IFAT) using fixed whole *Lawsonia* antigen on 96-well polystyrene microtitre plates and FITC-labeled antibodies directed against porcine IgG (Knittel et al 1998). The IFA test was modified slightly by using FITC-labeled antibodies directed against porcine IgM and IgA. This modified procedure was used to detect these antibodies, in addition to IgG, in each sow's colostrum for determining the concentration of different *Lawsonia*-specific immunoglobulins. The colostrum was diluted 2-fold in duplicate in PBS and transferred (100 µl/well) to two sets of *Lawsonia* coated 96-well plates as mentioned above. The inoculated plates were allowed to incubate for 30 minutes at 37° C. and were then washed 3 times with PBS. An anti-swine IgM or IgA FITC-conjugated antibody (Kirkegaard and Perry Laboratories, Inc.) previously diluted 1:200 in PBS was added to the plates and then, incubation and wash steps were repeated. The titre of each specific anti-*Lawsonia* antibody was detected using UV microscopy. Percent IFAT positives and mean titre values for each immunoglobulin were calculated for group comparisons to determine the frequency and the level of IgG, IgM, and IgA colostrum antibodies present among sows.

References

1. Knittel et al. (1998) Am J Vet Res 59:722-726.

The invention claimed is:

1. A method of vaccinating an animal having anti-*L. intracellularis* antibodies comprising the step of administering to said animal a single effective dose of an attenuated modified live *L. intracellularis* at day 1 to day 9 of age, wherein said single effective dose induces an effective humoral and cell mediated immune response when administered to said animal a single time.

2. The method of claim 1, wherein said animal is vaccinated at day 1 to day 6 of age.

3. The method of claim 1, wherein said animal is vaccinated at day 1 or 2 of age.

4. The method of claim 1, wherein said animal having anti-*L. intracellularis* antibodies has a detectable anti-*L. intracellularis* antibody titre of at least 1:4 per ml serum or fluid.

5. The method of claim 1, wherein said animal having anti-*L. intracellularis* antibodies has a detectable anti-*L. intracellularis* antibody titre of at least 1:64 per ml serum or fluid.

6. The method of claim 1, wherein said single effective dose comprises 3.0 TCID50 to 6.0 TCID50 of live modified *L. intracellularis* bacteria.

7. The method of claim 1, wherein the animals are birds, fishes, cattle, pigs, horses, and primates.

8. The method of claim 7, wherein the animals are pigs.

9. The method of claim, 1, wherein said animal is vaccinated at day 1 to day 4 of age.

10. A method of vaccinating an animal having anti-*L. intracellularis* antibodies consisting essentially of the step of administering to said animal a single effective dose of an attenuated modified live *L. intracellularis* at day 1 to day 9 of age, wherein said single effective dose induces an effective humoral and cell mediated immune response when administered to said animal at a single time.

11. A method of vaccinating an animal having anti-*L. intracellularis* antibodies comprising the step of administering to said animal a single effective dose of an attenuated modified live *L. intracellularis* at day 1 to day 9 of age, wherein said single effective dose induces an effective humoral and cell mediated immune response when administered to said animal at a single time and wherein said single dose provides the animal with increased protection against *L. intracellularis*.

* * * * *